(12) United States Patent
Mazzio

(10) Patent No.: US 8,964,286 B2
(45) Date of Patent: Feb. 24, 2015

(54) SYSTEM AND DEVICE FOR NON-DESTRUCTIVE RAMAN ANALYSIS

(71) Applicant: Hologic, Inc., Bedford, MA (US)

(72) Inventor: Victor Mazzio, West Chester, PA (US)

(73) Assignee: Hologic Inc, Bedford, MA (US)

( * ) Notice: Subject to any disclaimer, the term of this patent is extended or adjusted under 35 U.S.C. 154(b) by 0 days.

(21) Appl. No.: 14/221,418

(22) Filed: Mar. 21, 2014

(65) Prior Publication Data

US 2014/0204373 A1 Jul. 24, 2014

Related U.S. Application Data

(60) Continuation-in-part of application No. 13/541,883, filed on Jul. 5, 2012, now abandoned, which is a division of application No. 12/179,251, filed on Jul. 24, 2008.

(51) Int. Cl.
| | |
|---|---|
| *G02B 21/00* | (2006.01) |
| *G01J 3/02* | (2006.01) |
| *G01J 3/44* | (2006.01) |
| *G02B 21/24* | (2006.01) |
| *G01N 21/65* | (2006.01) |

(52) U.S. Cl.
CPC ............. *G01J 3/0218* (2013.01); *G01J 3/44* (2013.01); *G01J 3/0256* (2013.01); *G02B 21/24* (2013.01); *G01N 21/65* (2013.01); *G01J 3/0291* (2013.01); *G01J 3/02* (2013.01); *G01J 3/0202* (2013.01); *G01J 3/021* (2013.01); *G01J 3/4412* (2013.01); *G01J 3/0208* (2013.01); *G01J 3/027* (2013.01)
USPC ............................ 359/368; 359/393; 356/301

(58) Field of Classification Search
None
See application file for complete search history.

(56) References Cited

U.S. PATENT DOCUMENTS

| | | | |
|---|---|---|---|
| 4,744,642 A | 5/1988 | Yoshinaga | |
| 5,235,457 A | 8/1993 | Lichtman | |
| 5,764,365 A | 6/1998 | Finarov | |
| 7,095,032 B2 | 8/2006 | Montagu et al. | |
| 7,564,625 B2 | 7/2009 | McLeod | |
| 2005/0024721 A1 | 2/2005 | Storz | |
| 2007/0236786 A1 | 10/2007 | McLeod | |

OTHER PUBLICATIONS

ThermoFisher Scientific Customer Training Manual, The Basics of Raman Spectroscopy.
Nicolet Instrument Almega Visible Raman Spectrometer User's Guide.

*Primary Examiner* — Derek S Chapel

(57) ABSTRACT

A Raman microspectrometer system extends the optical reach and analysis range of an existing Raman microspectrometer to allow analysis and/or repair of an oversized sample. The Raman microspectrometer system includes an extender for extending the optical reach of the existing microspectrometer and a supplemental stage which extends the analysis range of the existing microspectrometer by providing travel capabilities for non-destructive analysis of an entire oversized sample. Such an arrangement decreases manufacturing costs associated with testing oversized samples such as mammography panels, enabling analysis and/or repair to be performed without destruction.

20 Claims, 13 Drawing Sheets

SYSTEM AND DEVICE FOR NON-DESTRUCTIVE RAMAN ANALYSIS

CROSS-REFERENCE TO RELATED APPLICATIONS

This application is a continuation-in-part and claims priority under 35 U.S.C. §120 to U.S. patent application Ser. No. 13/541,883, filed Jul. 5, 2012, which is a divisional of U.S. patent application Ser. No. 12/179,251, filed Jul. 24, 2008. Each of the above applications is hereby incorporated by reference.

FIELD OF THE INVENTION

This invention relates generally to the field of micro-spectrometry and more particularly to a non-destructive method and apparatus for identifying, analyzing and repairing digital imaging panels using a microspectrometer.

BACKGROUND OF THE INVENTION

FIG. 1 illustrates a typical Raman microspectrometer 10. The Raman microspectrometer 10 includes an optical microscope 20, coupled via supports 32 and 34 to a combined excitation laser source/spectrometer 30. The Raman microspectrometer is used to analyze the molecular structure of a sample that is disposed on the microscope stage 22. During analysis the sample is secured to the stage 22 and laser beam pulses are directed via the optical transfer tube 33 through the lens of the microscope 20 onto points in the sample. Resulting Raman and Rayleigh scatter from the sample is forwarded back through the microscope lens and optical transfer tube 33 to the spectrometer. The spectrometer filters out the Rayleigh scattered energy and separates the wavelengths of the Raman scattered energy to identify the molecular structure at examined points of the sample.

The stage 22 on which the sample is disposed is motor controlled by the joystick 15 to provide movement (i.e., travel) of the stage along the x, y and z axis to thereby allow analysis of each point in the sample. In general, the size of the stage is designed to accommodate slides and/or semiconductors or other types of samples for which Raman Microspectroscopy has been shown to be appropriate. For example, the stage of the microspectrometer in FIG. 1 has a four inch by four inch x/y travel capability, which is generally sufficient to examine any sample that fits within the stage.

However it is sometimes desirable to perform Raman analysis on samples having a size that exceeds that of an existing optical microscope stage. An example of such a sample is a digital mammography panel that is used in x-ray imaging systems, also referred to as a flat panel detector. Flat panel detectors may be comprised of a thin film transistor layer coated with one or more material layers including a photoconductive layer such as amorphous selenium. Exemplary layers of a flat panel detector 50 are shown in FIG. 2 to include a top electrode 52, a charge barrier layer 53 (typically made of Parylene-N) separating the top electrode from an amorphous selenium-based charge generator layer 54, and a charge collection electrode layer 55 disposed upon a thin-film transistor ("TFT") array 56.

Under normal operation, before exposure to x-ray radiation, the photoconductive layer is uniformly biased relative to electrical charge readout means by application of a biasing field via voltage source 58. As x-rays are directed at the panel, electrons move from the valence band to the conduction band thereby creating holes where electrons once resided. Electron-hole pair charges move in opposite directions along electric field lines towards opposing surfaces of the photoconductive layer. Holes collected by the electrode 55 are used to charge capacitors in the TFT array 56 which may subsequently be read out to provide a latent image.

The accuracy of image capture is thus highly dependent upon the ability of the electron hole pairs to travel freely within the photoconductive layer. However anomalies in the manufacturing process may give rise to defects within the amorphous selenium that impair the free movement of electron hole pairs. For example, temperature changes or other processing procedures may cause crystals to be generated in the selenium. Before the panel may be released for commercial use, it is necessary to perform a series of tests on the panel to ensure that the panel is free from such anomalies.

Panel testing may identify spatial coordinates of one or more problems in the panel. A Raman microspectrometer is preferably used to determine the molecular structure at the coordinate of interest. However it is difficult to use existing Raman microspectrometers to analyze digital image panels in their entirety because the size of the flat panel cannot be accommodated by the existing stage and travel capabilities of the microspectrometer. Digital mammography panels may measure more than eleven by nine inches, while the travel distance of available microspectrometer stages are only ( ) four inches or less in each dimension. In addition, even if the travel of the existing stage could be adjusted, the physical space constraints between the microscope 20, optical transfer tube 33, and spectrometer 30 limit the ability to properly examine the entire panel.

As a result, inspection of problem coordinates of a mammography panel requires destruction of the panel. Panels are cut into discrete sections that can be examined using the current stage travel capabilities. After destruction, a technician would iteratively step through each pixel position of each panel section to locate and analyze anomalies caused by the manufacturing processes. This process was time consuming, destructive and concomitantly expensive. It would be desirable to identify a non-destructive apparatus and method for analyzing oversized samples using micro spectrometers.

SUMMARY OF THE INVENTION

According to one aspect of the invention, an extender for extending an optical reach of a microspectrometer includes a housing including a proximal orifice, a distal orifice and a mounting plate for attaching the housing to a microscope of the microspectrometer such that a lens of the microscope is aligned with the proximal orifice. A plurality of minors is positioned within the housing to provide an optical channel between the proximal orifice and the distal orifice of the housing to thereby extend the optical reach of the microspectrometer. The addition of the extender to the microspectrometer thus enables oversized samples to be analyzed, repaired and returned to production without destruction.

According to another aspect of the invention, a supplemental stage for use with a microspectrometer having an existing stage is provided. The supplemental stage includes a tray for supporting an oversized sample and a motorized travel system for controlling a travel movement of the tray in at least one of an x and y direction, wherein the oversized sample exceeds the travel capabilities of the existing stage in at least one of the x and y directions, and wherein the travel capabilities of the motorized travel system are at least matched to the x and y dimensions of the oversized sample. In addition, a controller couples a stage controller of the microspectrometer to the motorized travel system. With such an arrangement, software tools of the microspectrometer may easily be used when analyzing an oversized sample.

According to a further aspect of the invention, a microspectrometer system for non-destructive analysis of an oversized sample includes a microspectrometer comprising an optical microscope coupled to a spectrometer by an optical transfer tube, where the optical microscope includes a lens and an existing stage. An extender is removably coupled to the optical microscope. The extender has a proximal orifice disposed adjacent to the lens and a distal orifice, where the extender extends an optical reach of the microscope to the distal orifice. The system further includes a supplemental stage, coupled to a controller of the stage of the optical microscope, for moving the oversized sample along a travel distance in at least one of the x and y dimensions that exceeds a travel capability of the existing stage of the optical microscope in a corresponding dimension. Such an arrangement enables an oversized sample, such as a digital mammography panel, to be analyzed without destruction. As will be described in further detail below, an additional advantage of the present invention is that it allows Raman analysis to be performed at an earlier stage in the manufacturing process; rather than being used only to investigate defects of destructed panels, Raman analysis may be used to analyze and repair defects, allowing panels to be returned to production, thereby greatly reducing the cost associated with mammography panel manufacturing.

DETAILED DESCRIPTION

According to one aspect of the invention, an improved Raman microspectrometer system extends the optical reach and analysis range of an existing Raman microspectrometer to allow analysis and/or repair of an oversized sample. For the purposes of this application, an oversized sample shall mean any sample that exceeds the travel capabilities of an existing stage of the existing Raman microspectrometer in any one of an x, y or z dimensions. The improved Raman microspectrometer system includes an extender for extending the optical reach of the existing microspectrometer and a supplemental stage which extends the analysis range of the existing microspectrometer by providing travel capabilities for non-destructive analysis of an entire oversized sample. Such an arrangement decreases manufacturing costs associated with testing oversized samples such as mammography panels, enabling analysis and/or repair to be performed without destruction. In addition, as will be described further below, such an arrangement increases the speed and accuracy of defect analysis and repair because it allows coordinate information received from a panel testing procedure to be used by software to quickly and accurately pinpoint problem areas in the panel.

Figure 1:
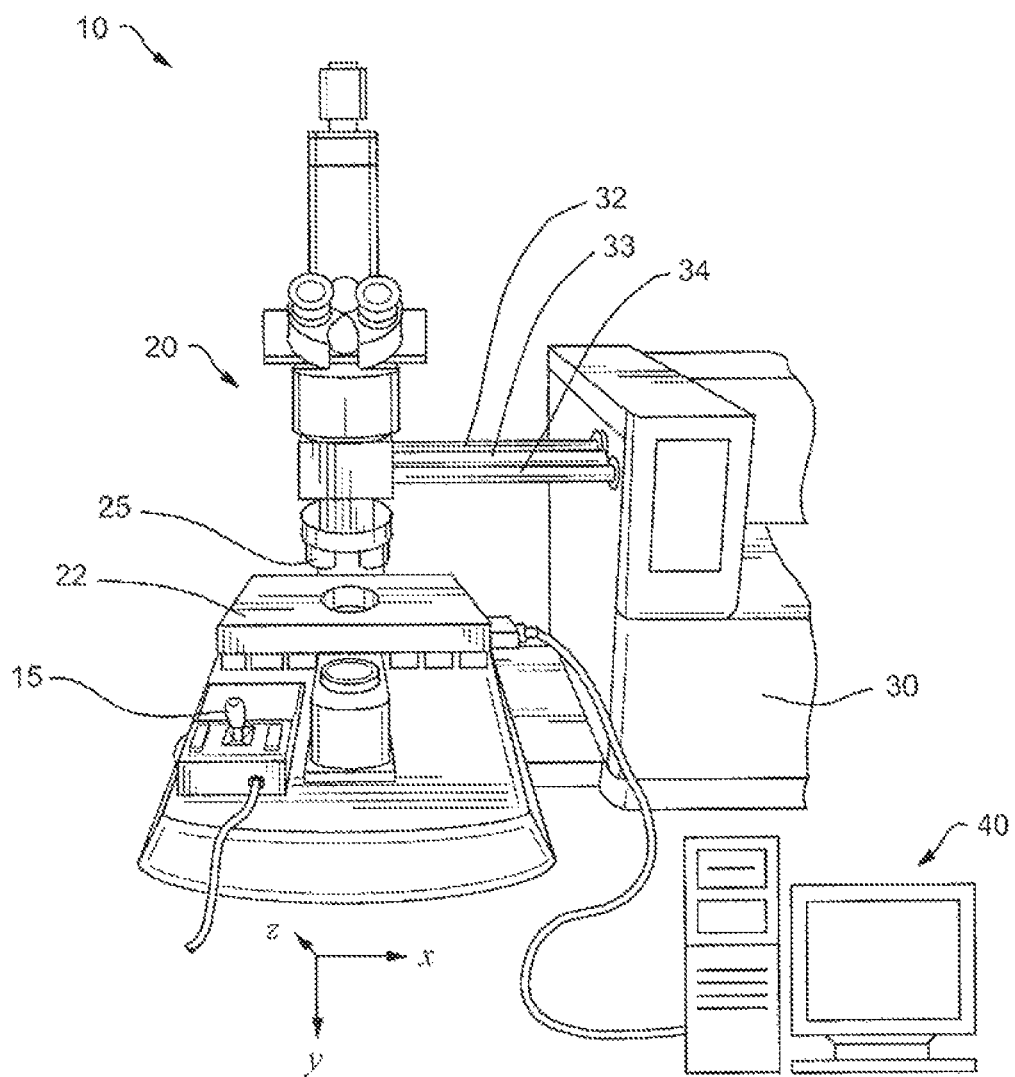
FIG. 1 is a diagram illustrating a prior art Raman microspectrometer.
Figure 2:
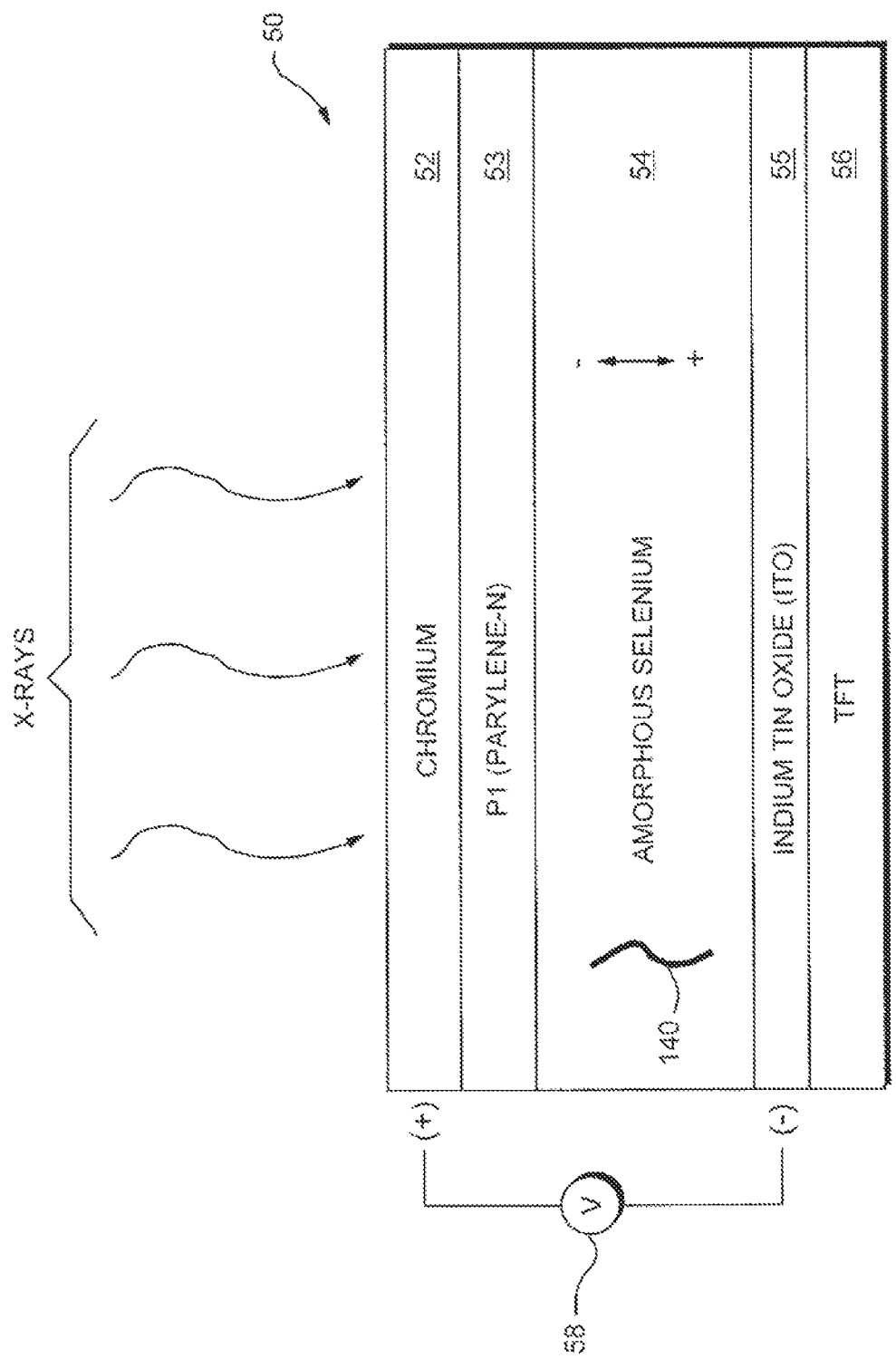
FIG. 2 is a cross section illustration of an exemplary digital mammography imaging panel.
Figure 3:
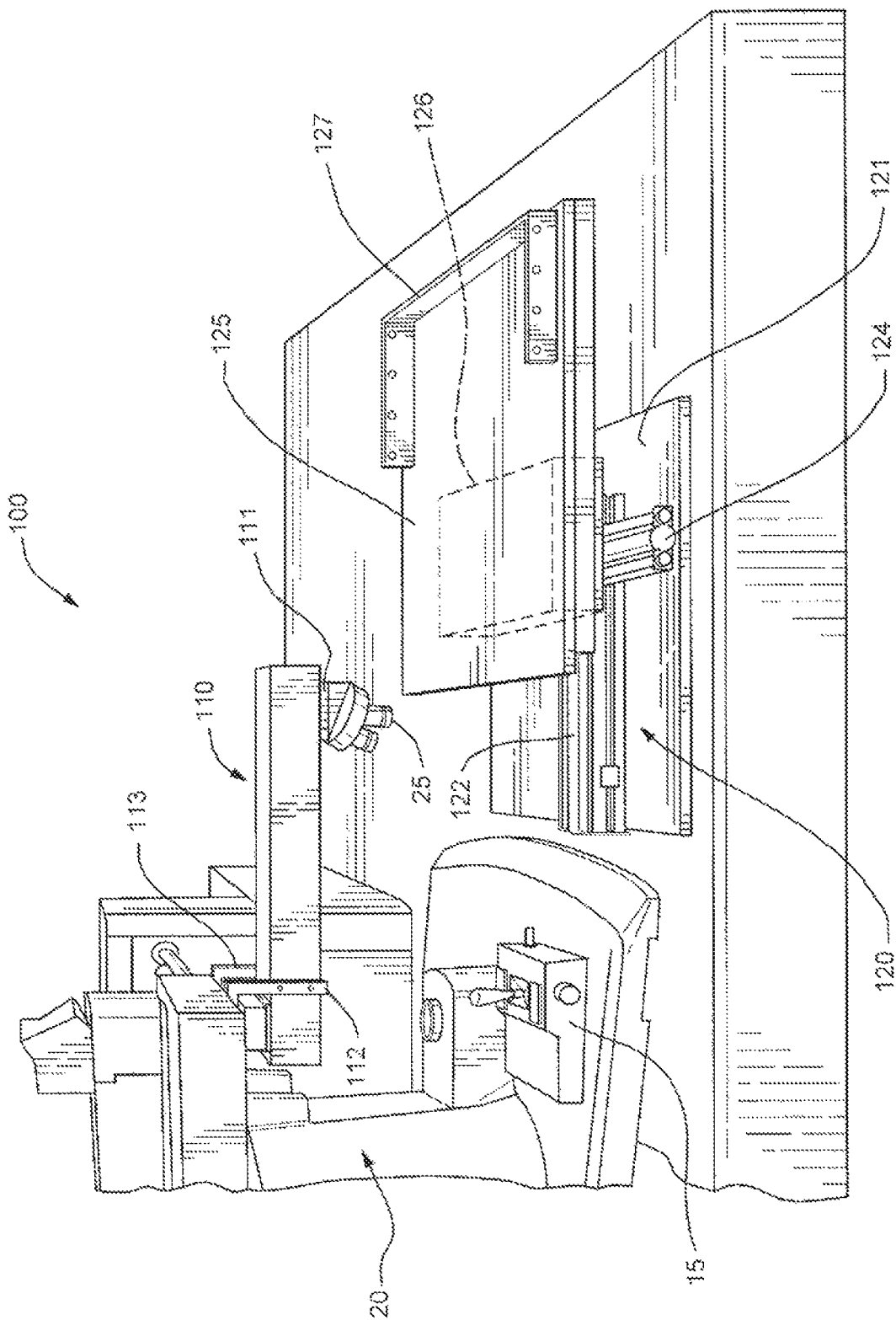
FIG. 3 is a diagram of an improved Raman microspectrometer system of the present invention for use in analyzing and/or repairing oversized samples such as mammography imaging panels.

FIG. 3 illustrates one embodiment of a Raman microspectrometer system 100 of the present invention. The embodiment 100 includes an extender 110 which removably mounts onto an optical microscope 20. In a preferred embodiment, the extender 110 includes, or has attached thereto, a coupling device (such as a mounting plate) adapted for connection to a turret mount of the microscope 20 (not shown). The mounting plate allows the extender to easily attach to the microscope in place of the turret 25. In FIG. 3 the extender is shown to extend generally perpendicular to a y axis defined by the microscope although this is not a requirement of the invention.

The extender includes a housing having a proximal orifice (not viewable in FIG. 3) which is positioned to receive light from the optical microscope lens when the extender is attached to the optical microscope. The housing also includes a distal orifice which is positioned to enable the light waves from the optical microscope to be directed towards a sample to be analyzed. For example, in the arrangement of FIG. 3, the housing comprises an upper surface and a lower surface, the proximal orifice extends into the housing through the upper surface and the distal orifice extends into the housing at the distal end of the lower surface. As will be described in further detail with regard to FIGS. 5-7, two or more minors are disposed within the housing for directing light waves between the lens of the optical microscope and a sample that is positioned below the distal orifice.

In one embodiment, optical signals pass between minors via a fluid. The fluid may include air as well as other gases, such as helium, nitrogen, argon, etc. Other waveguide materials having various refractive indices known to those of skill in the art may be substituted herein without affecting the scope of the invention. Such materials include but are not limited to plastic, liquid or glass fiber or bundle of fibers.

A turret mount 111 may advantageously be positioned over the distal orifice to enable attachment of a turret 25 comprising one or more magnification lenses into the optical path. Although a turret is shown, it should be appreciated that the design allows any lens arrangement to be used at the distal orifice, and the present invention is not limited to the use of a lens turret.

One or more suspension arms 112, 113 may be used to provide further support for the housing. It can be appreciated that the extender adds an additional, unanticipated weight to the turret mount of the optical microscope which may not have been anticipated by the designer of the microscope; the suspension arms may be used to relieve stress on the turret mount that is caused by the added weight of the extender. In the embodiment of FIG. 3, the suspension arms 112, 113 are mounted and designed in accordance with a shape of the body of the microscope to enable the suspension arms to hang from the lens housing of the optical microscope. It should be noted that the illustrated embodiment is representative of only one manner of relieving stress on the turret mount, other methods of bracing known in the art are considered as equivalents to the suspension arms and thus within the scope of the present invention. It should further be noted that the suspension arms are advantageous, but not a necessary element of the present invention.

The improved Raman microspectrometer system 100 also includes a supplemental stage 120. The supplemental stage 120 is a motorized stage adapted to travel in an x and y direction along tracks 122 and 124. A motor 126 is disposed above the rails to control the movement of the tray in the x and y direction, and further includes a lift mechanism for movement of the stage in the z direction.

The supplemental stage 120 further includes a tray 125 which is used to mount and secure the sample for analysis and/or repair. In general the size of the stage and the length of the rails should be selected to support and allow complete analysis of the desired oversized sample. For example, a supplemental stage for analysis and/or repair of digital mammography panels may have a z dimension travel of one inch and include 12 inch horizontal and vertical rails upon which is mounted a 12"×12" tray.

In the embodiment of FIG. 3 the supplemental stage 120 is shown mounted on a support panel 121 which disperses the overall weight of the system to control tipping or other movement of the system during operation. In FIG. 3 the tray is shown to include a mount 127 for securing a digital mammography panel to the tray. In one embodiment, the tray 125 may be swappable to accommodate different sizes and types of oversized samples using a common travel system.

According to one aspect of the invention, movement of the supplemental stage is controlled by the joystick 15 of the existing stage 22 via a Programmable Multi-Access Controller (PMAC) or similar device having the power to drive a larger stage. The PMAC may accept both manual input (i.e., from joystick 15) and computerized input (i.e., from system software). The PMAC is thus used to move the tray to position a coordinate of the sample beneath the extended optical path. As will be described in more detail later herein, software drivers cooperate to coordinate travel of the supplemental stage and analysis of the oversized sample such that existing software analysis tools can be used without modification.

There are several benefits provided by the system of the present invention. Extending the optical reach of a Raman microscope beyond its manufactured position increases its overall utility by eliminating sample size limitations associated with physical constraints of the microspectrometer components. The use of the microspectrometer is therefore not limited to merely post-destruction investigation of defects, but now may be integrated into a panel verification and repair process.

Figure 4:
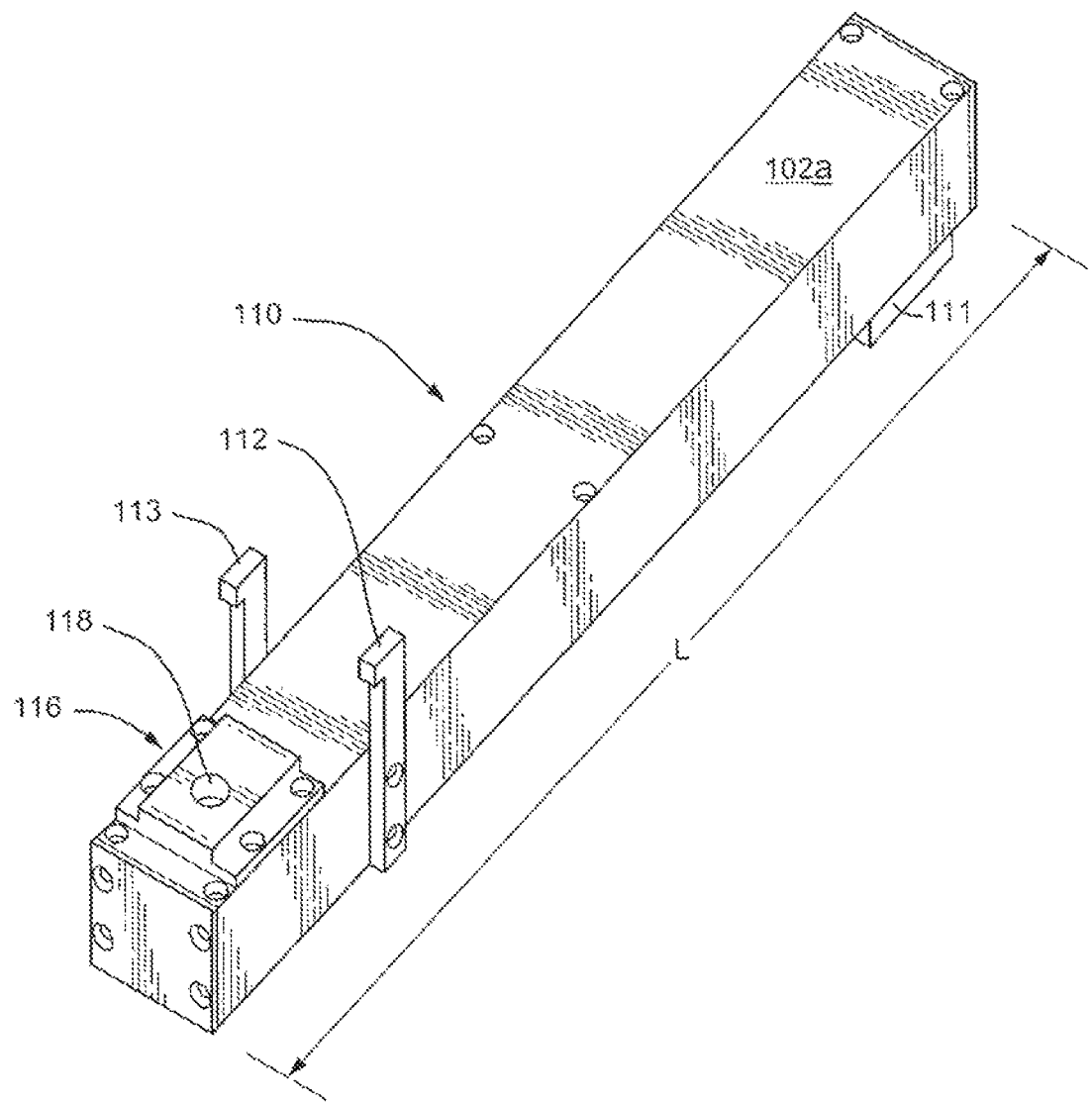
FIG. 4 is a diagram of a Raman microscope extender of the present invention.

FIG. 4 illustrates the exemplary extension 110 in increased detail. In this embodiment, the extension comprises a rectangular housing formed of aluminum with a black anodize finish. A stainless steel mounting plate 116 having an opening extending there-through is positioned on a top surface 102A over the proximal orifice 118. Suspension arms 112, 113 are affixed to the sides of the housing, proximate to the mounting plate, to provide additional support and relief of stress to the mounting plate/turret mount pair. A turret mount 111 (or other lens mounting coupling device) is positioned on a bottom surface 102B (not shown) of the extender. In general the turret mount 111 (or other lens mount) may conform to the turret mount of the microscope 20 although this is not a requirement, and it is appreciated that there are a variety of turrets available in the art. Further, although the mounting plate 116 and turret mount 111 are shown as welded pieces for the extension, in other embodiments it is envisioned that one or more of the turret mounts and mounting plates may be removable to facilitate use of the extender 110 with different microscopes and turrets. In addition, although the mounting plate 116 is shown fixed to the extender 110, other embodiments are envisioned wherein the mounting plate rotates around the proximal orifice to enable rotation of the extender 110.

As will be discussed in more detail later herein it should be appreciated that FIG. 4 illustrates only an exemplary embodiment, and multiple different extension embodiments capable of extending an optical reach are contemplated. For example, although a generally rectangular shape is shown the present invention is not limited to the extension having any particular shape characteristics; for example the extension may be shaped as a tube, or include fewer or greater angles. Although the extension is shown comprised of multiple mated pieces, it is appreciated that various parts, or all, of the extension may comprise a unitary piece. Although the extension of FIG. 4 is shown as a fixed, rigid piece, as will be described later herein other embodiments, wherein the extension is flexible, telescoping or rotatable are contemplated. Although certain finishes and materials are described, there are no particular limitations to the material or finish of the extension. In short, any device that is capable of establishing an optical channel between a first orifice and a second orifice can be substituted herein without affecting the scope of the present invention.

Figure 5A:
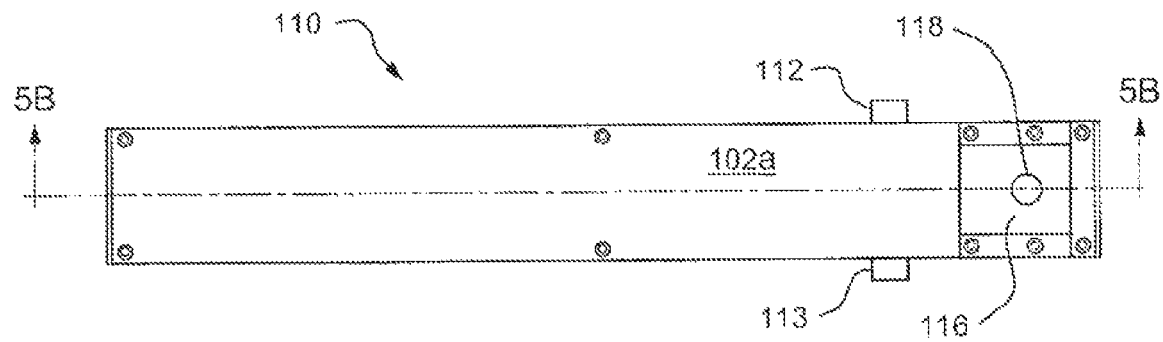
FIG. 5A is a top perspective view of the Raman microscope extender of FIG. 4.
Figure 5B:
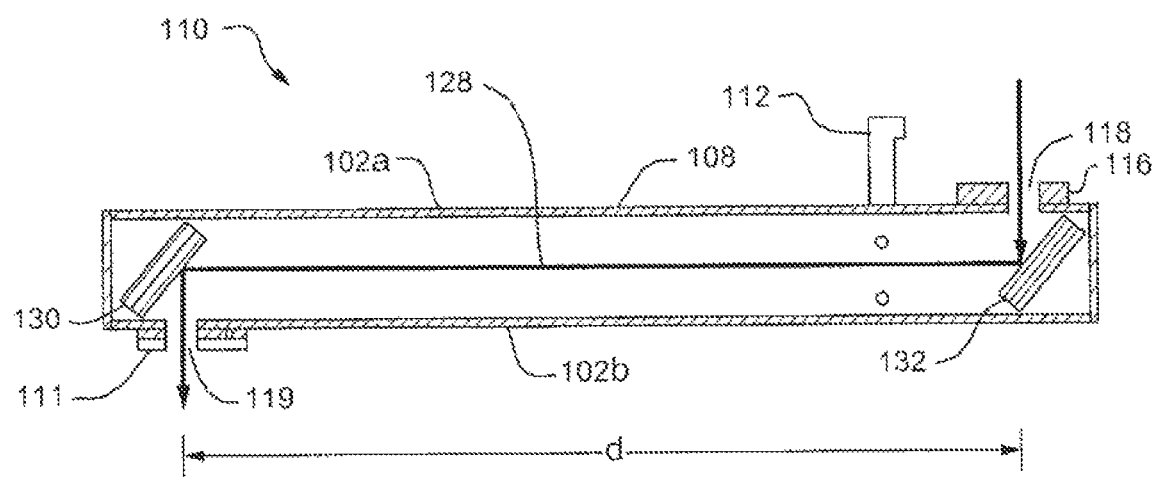
FIG. 5B is a cross section view of the Raman microscope extender taken along line B of FIG. 5A.

FIGS. 5A and 5B comprise top perspective view and a cross section view of the extender 110. The cross section view of FIG. 5B is taken along line B of FIG. 5A. As shown in FIG. 5B, at least a pair of mirrors is positioned inside the housing. In a preferred embodiment, each of the mirrors is positioned at a 45 degree angle relative to its opposing orifice. The proximal mirror 132 is positioned to exchange light waves between the lens of the microscope and the distal minor 130. The distal minor is positioned to exchange light waves between the proximal minor 132 and the sample (not shown). The interior walls of the housing 108 are preferably coated with a non-reflective coating. Together the orifices, 118, 119, housing 108 and mirrors 132 and 130 define an optical channel for performing Raman analysis.

Figure 6:
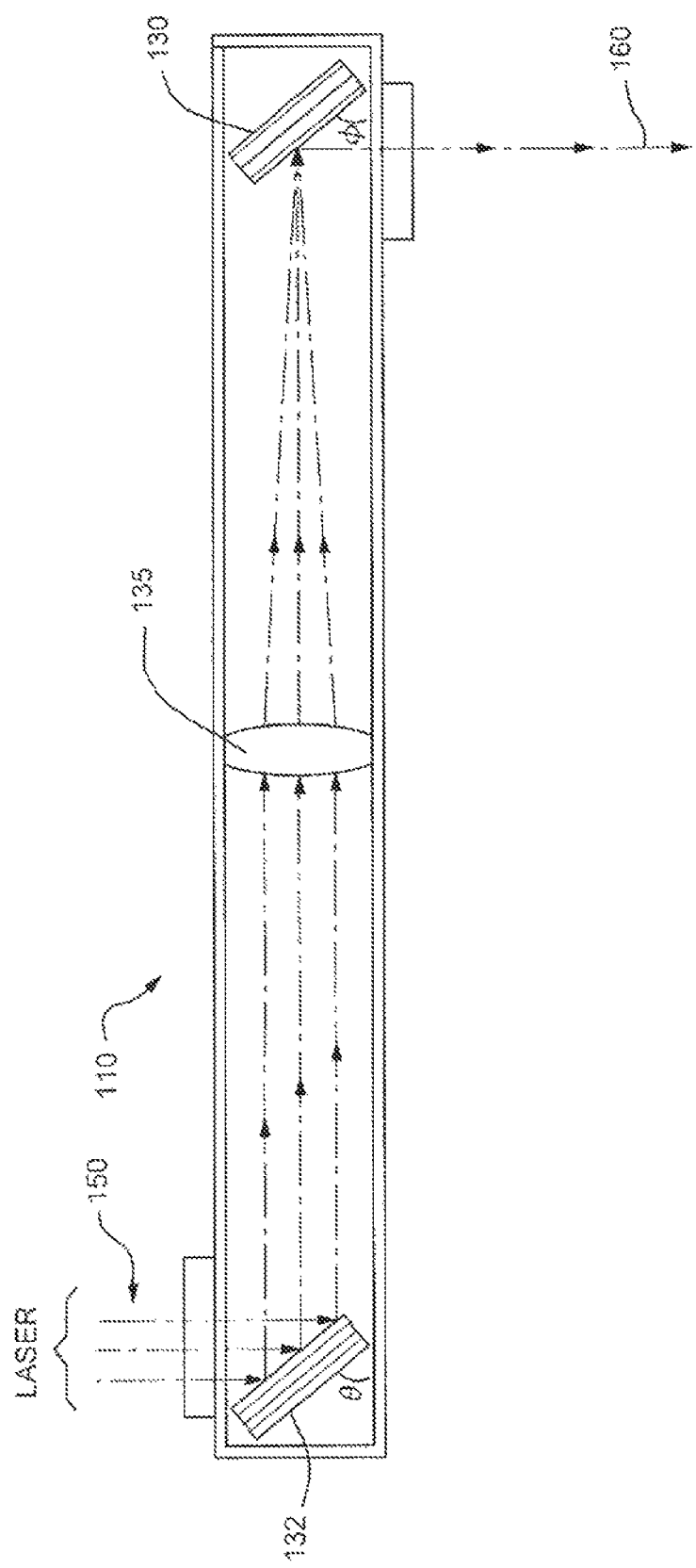
FIG. 6 is cross section view of the Raman extender illustrating a path of laser pulses through the extender.
Figure 7:
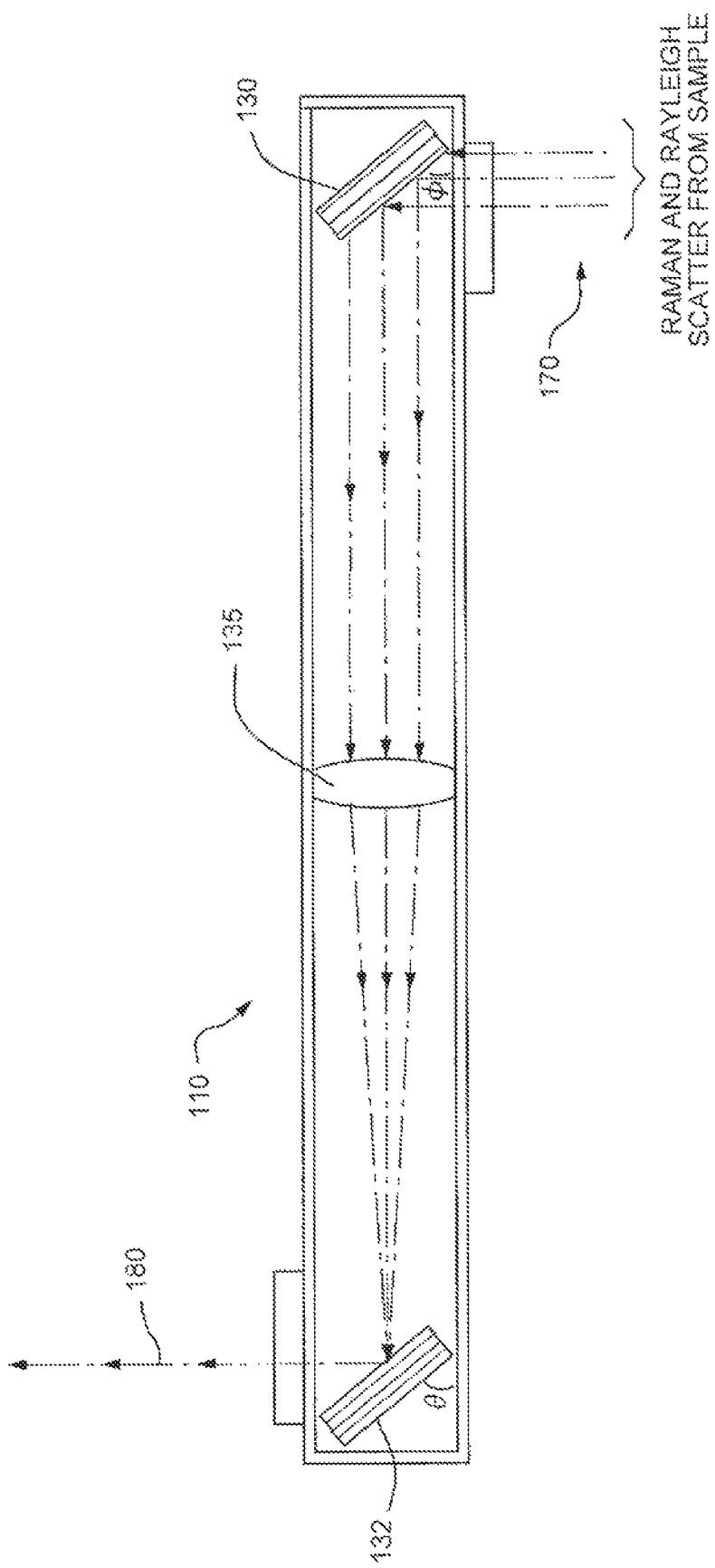
FIG. 7 is a cross section view of the Raman extender illustrating a return path of Rayleigh and Raman scatter from a sample to the Raman microspectrometer.

FIG. 6 is cross section perspective of the Raman extender 100 provided to illustrate the flow of light pulses from the laser source to the sample. In the embodiment of FIG. 6, an optional condensing lens 135 is disposed between minors 132 and 130 for focusing dispersed light waves from the laser onto a fixed point of the mirror 130. As is known in the art, the application of the laser light pulse to the sample causes resonance of the sample which results in Rayleigh and Raman scatter light. As shown in FIG. 7, the Rayleigh and Raman scatter is returned to the extender and reflected by minor 130 onto condensing lens 135, which focuses the scatter onto minor 132. Minor 132 directs the scatter to the spectrometer for molecular analysis.

Figure 8:
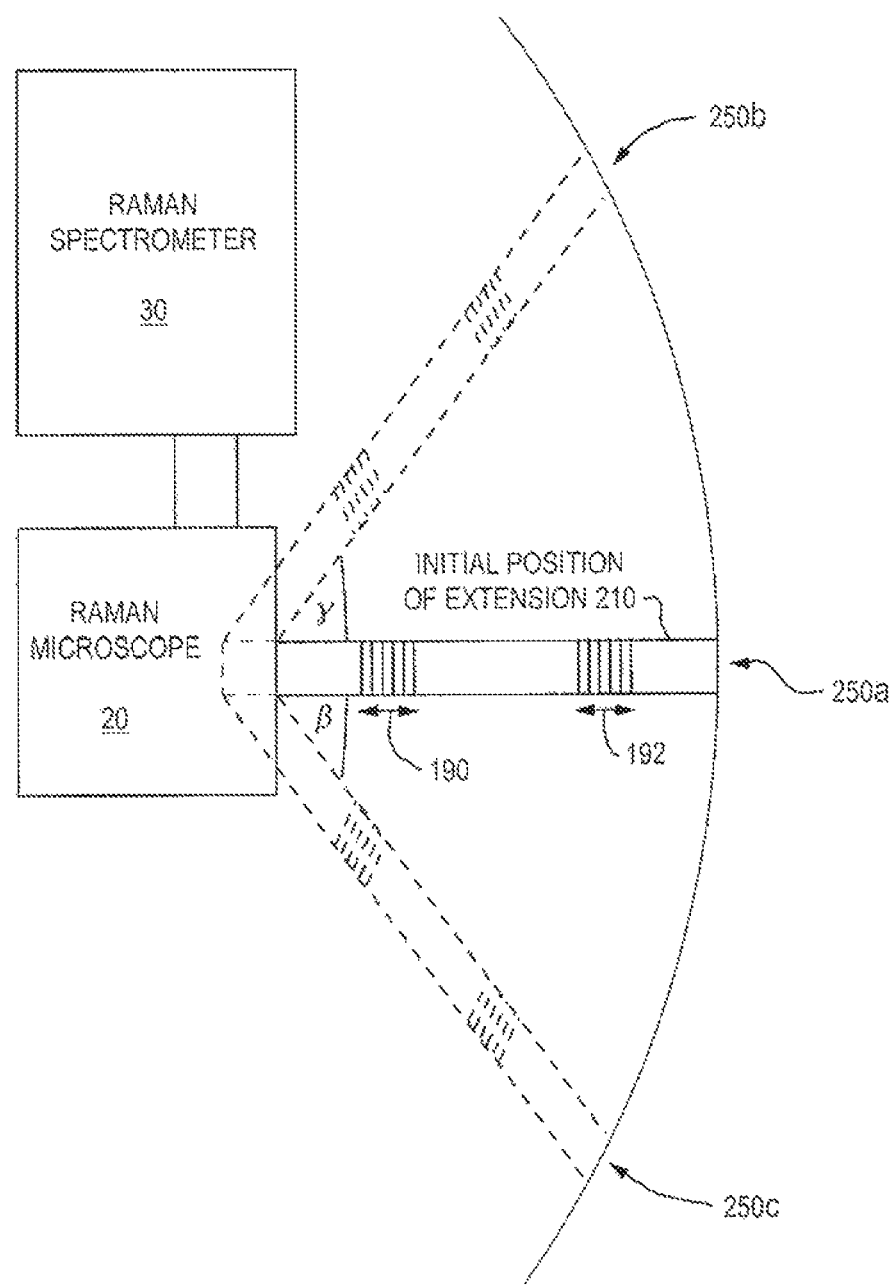
FIG. 8 is a top down view of a Raman microscope, spectrometer and extender of the present invention, illustrating various different positions and embodiments of the extender.

FIG. 8 is a top perspective view of alternate embodiments of the present invention in which the extender 110 is moveable. Movement of the extender 110 may be manually, or may be software controlled. For example, the mounting plate 116 (not shown) which couples the extender to the microscope may be rotatably software controlled to move the distal end of the extender to various positions along the x plane. In one embodiment, the extender comprises one or more bellows 190, 192, which enable telescoping of the extender, to extend or retract its length along the x-axis. In one embodiment of the invention, the movement of the extender is coordinated with movement of the supplemental stage, although it is not required that the two pieces move in concert. It can be appreciated, however, that such an arrangement increases the ability of the system to thoroughly analyze the sample and accommodate for different space constraints in a laboratory environment.

Figure 9:
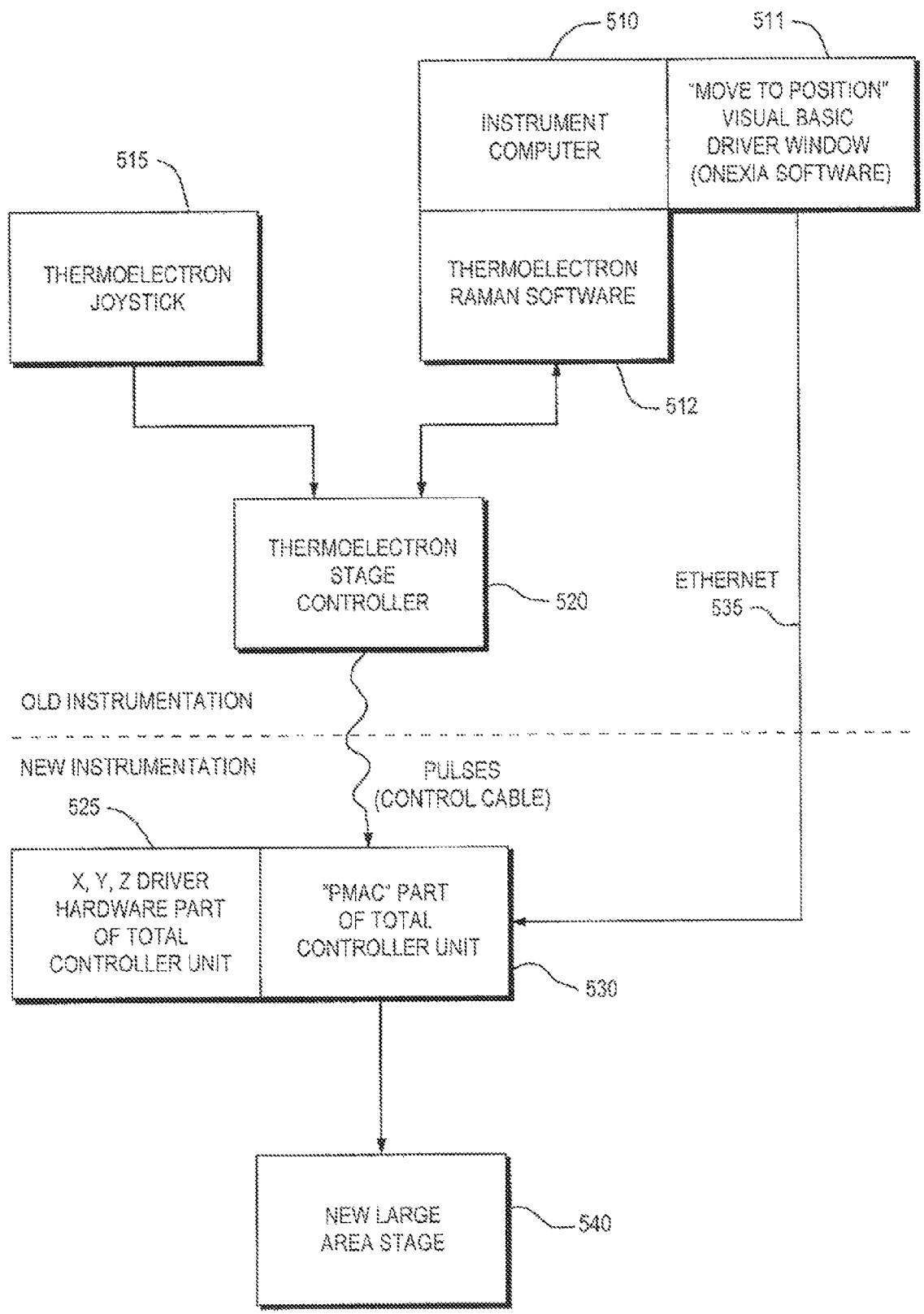
FIG. 9 is a block diagram illustrating exemplary software components of the improved Raman microspectrometer system of the present invention.

FIG. 9 is a block diagram illustrating functional blocks of a control system for the improved Raman microspectrometer of the present invention. The functional blocks may be implemented in software, hardware or a combination thereof. An instrument computer 510 includes a processor, display and user interface for performing spectral analysis of a sample. For example, the instrument computer provides an interface driver 511 that allows a user to input coordinates. Raman software 512 controls the application of laser pulses to the sample and displays the resultant frequency response. The stage may be moved in response to coordinate selection via control signals forwarded from an RS232 line to the stage controller 520. In addition, stage movement may be controlled manually by joystick 515. Movement signals from the joystick and the software 512 are interpreted by the stage controller 520.

In prior art designs, the output from the stage controller 520 was fed directly to the existing stage 22. However the present invention adds the Programmable Multi-Access Controller (PMAC) 530 which is used to drive the supplemental stage. The PMAC interprets movement information received either via the joystick 515 or directly from the driver 511 via Ethernet interface 535. The PMAC uses this information to identify an analysis coordinate of the oversized sample, and a travel driver 525 moves the sample to the desired coordinate. The positioning software 530, 525 thus interfaces with driver 511 to provide a positioning overlay that enables analysis of an oversized sample without modification of underlying Raman software 512.

Figure 10:
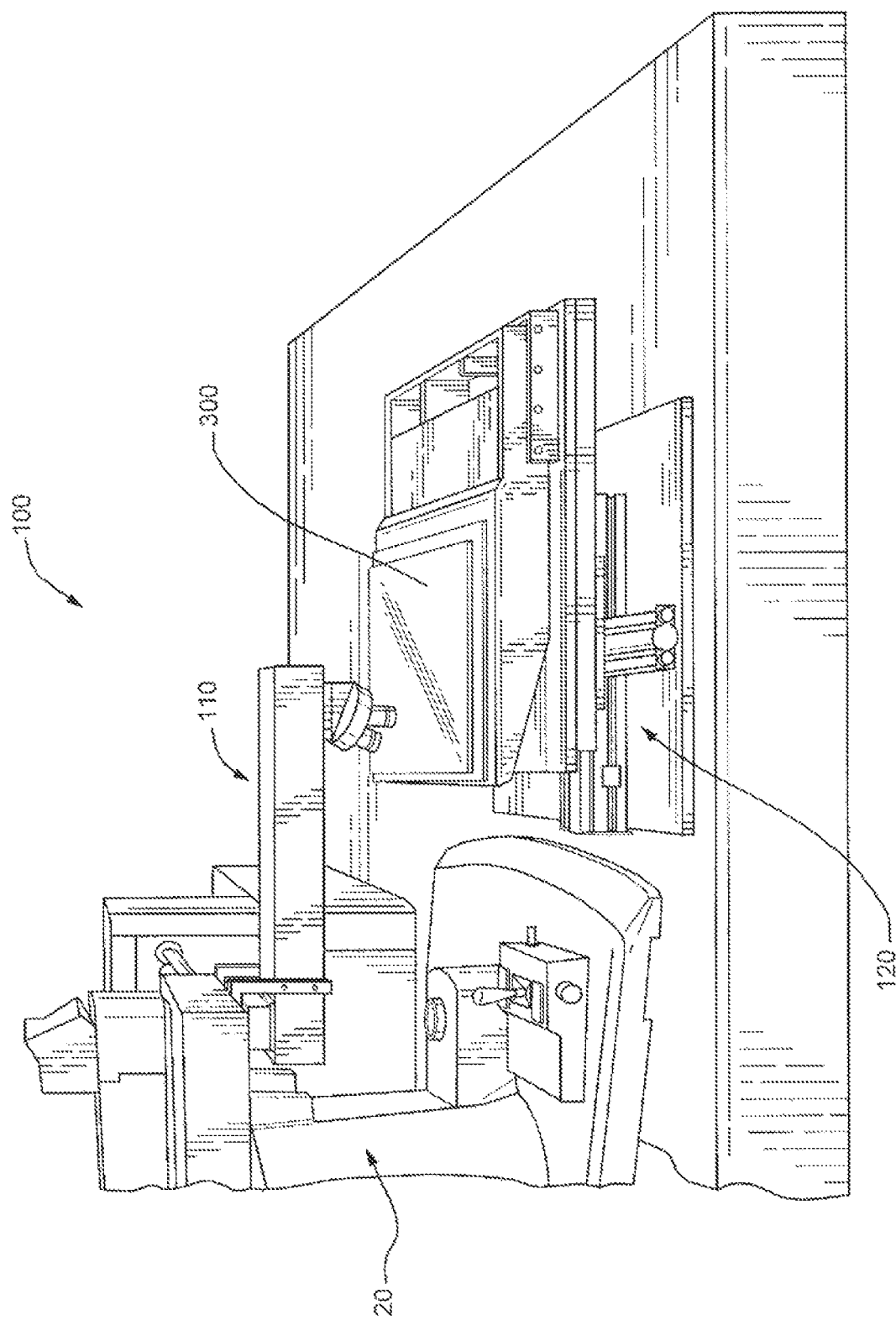
FIG. 10 is a diagram illustrating the analysis of a mammography panel using the improved Raman microspectrometer system of the present invention.
Figure 11:
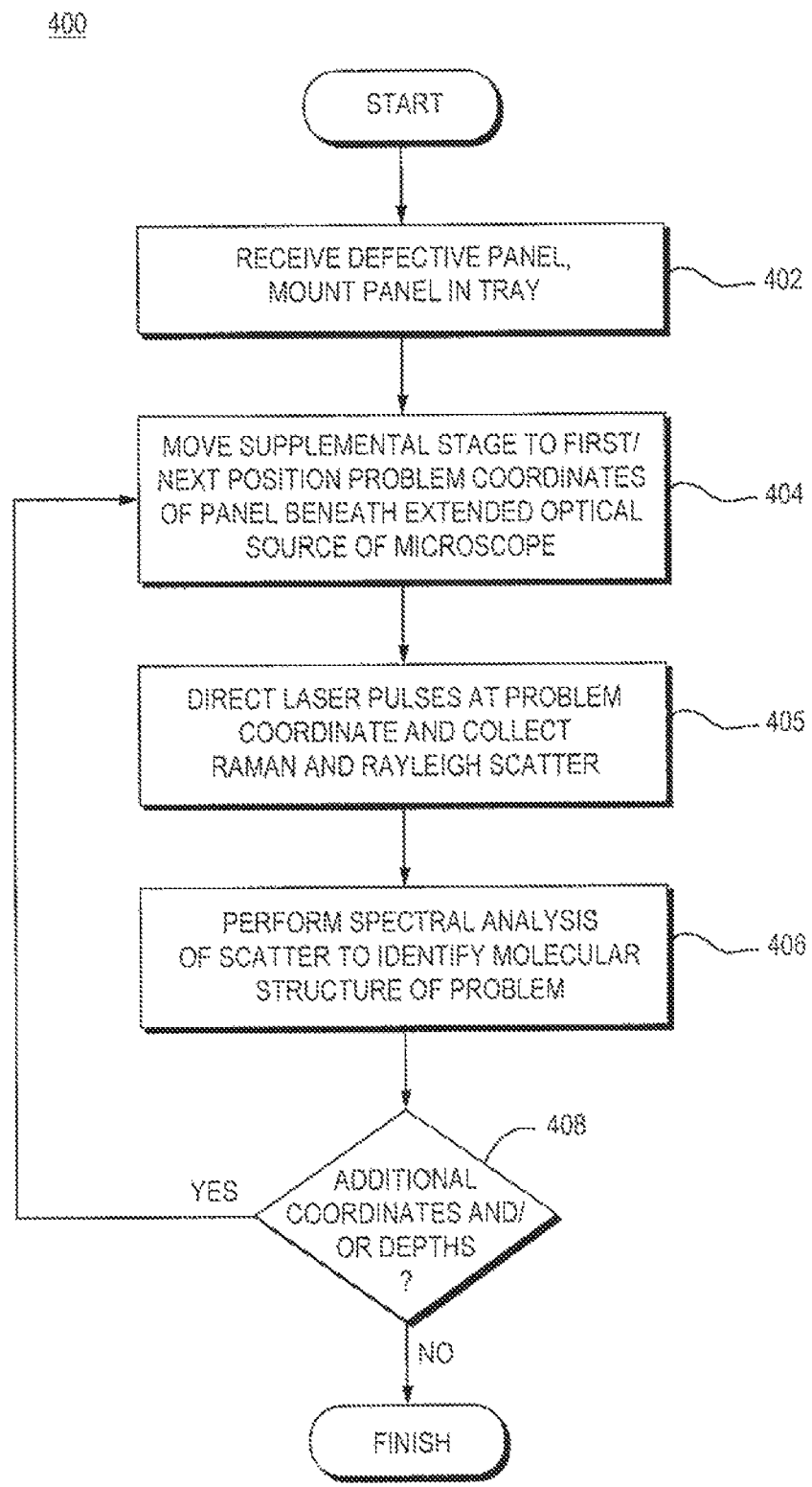
FIG. 11 is a flow diagram illustrating exemplary steps that may be performed in a defect analysis process for an oversized sample using the improved Raman microspectrometer of the present invention.
Figure 12:
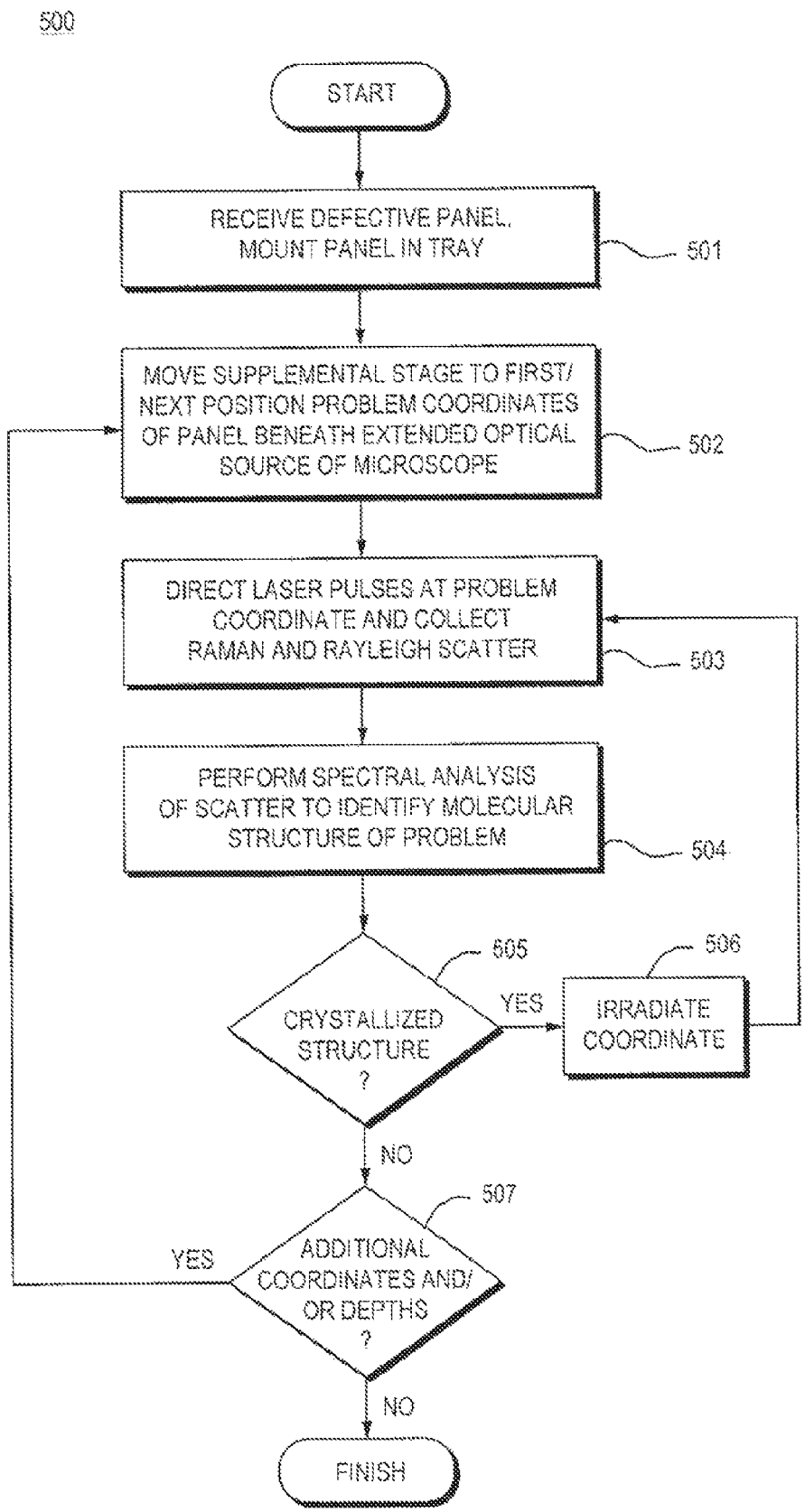
FIG. 12 is a flow diagram illustrating exemplary steps that may be performed in a defect analysis and repair process for an oversized sample using the improved Raman microspectrometer of the present invention.

FIG. 10 illustrates the improved Raman microspectrometer system of the present invention with a digital mammography panel 300 secured into tray mounts 127. As shown in FIG. 10, the entire mammography panel can be inserted into the tray 125, without the need to disassemble or otherwise deconstruct the panel. FIGS. 11 and 12 are flow diagrams which are provided to illustrate exemplary processes for analyzing and/or repair an oversized sample using the improved Raman microspectrometer of the present invention. For purposes of simplicity the processes will be described as directed at analysis and/or repair of a mammography panel, although the process is not limited to any particular type of oversized sample.

Referring now to FIG. 11, at step 402 a panel is received for analysis. The panel that is received may be a panel that is rejected by a manufacturing verification process as defective. In such embodiments, coordinates associated with one or more defects may be provided with the panel. During step 402, the panel is mounted in the tray, and the supplemental stage moves the panel to an initial location of the panel (for example, pixel 0,0).

At step 404 the supplemental stage moves the panel such that coordinates associated with the first defect are disposed beneath the distal orifice of the extender 110. At step 405, one or more laser pulses are directed at the sample. It should be noted that the ability to control z axis movement of the stage, in conjunction with the ability to manage the strength of the lens that is used allows analysis to be performed at different depths of the sample, thereby enabling a three dimensional molecular model of the structure to be built.

The laser light impinges upon a molecule of the sample and interacts with the electron cloud of the bonds of that molecule. The incident photon excites one of the electrons into a vibrational excited state, which generates Stokes Raman scattering. The Raman scatter together with Rayleigh scatter is returned on the optical channel to the spectrometer. At step 406 spectral analysis is performed on the scatter to identify the molecular structure of the sample. At step 408, it is determined whether there are additional coordinates and/or depths (at the same coordinate) that are to be analyzed. If so, the process returns to step 404 and the supplemental stage is repositioned.

The analysis is complete when all coordinates have been analyzed at all desired depths. Analysis can therefore be used to provide a multi-dimensional molecular information repository which can be used to identify manufacturing defects. Such defects may be, for example, additives that are erroneously deposited by an instrument during fabrication. Analysis can direct the manufacturers to investigate and correct process errors.

In addition the present invention can be used to correct certain identified defects and return the panels to the production line, thereby saving tens of thousands of dollars. For example, a common defect that is encountered in the mammography panel fabrication process is the crystallization of the amorphous selenium. Crystallization of selenium prohibits the free travel of holes and electrons in the selenium, thereby adding artifacts to resultant images. It is known in the art that amorphization of crystallized selenium can be achieved by application of a laser pulse having certain characteristics to the crystal structure. FIG. 12 illustrates exemplary steps that may be performed during an analysis and repair process of the present invention.

As in FIG. 11, at step 501 a panel is received from testing, placed onto the supplemental stage and the position of the stage is initialized. At step 502 the supplemental stage is moved to the first identified coordinate and laser pulses are directed at the coordinate. At step 504, spectral analysis of the Raman scatter is performed. At step 505 the frequency response associated with the Raman scatter is examined to determine whether the response indicates that the molecular structure is that of crystallized selenium. If it is determined that the structure is crystallized selenium, then at step 505 the molecule is irradiated to return the structure to amorphous. At step 503 the molecule may be examined to determine whether the irradiation was successful. The process continues until irradiation of each crystallized structure has been successfully completed.

In the embodiment in which a Raman microspectrometer includes an optical extender, the Raman microspectrometer is more sensitive to crystalline selenium (e.g., by being more sensitive to the molecular vibrations of crystalline selenium) in an amorphous selenium matrix compared to a Raman microspectrometer without an optical extender. Additionally or alternatively, the Raman microspectrometer with an optical extender is configured to be less sensitive to layers above or below the focal plane. The optical extender can be optionally configured to variably extend, e.g., extend fully or partially or not at all. The more extended the optical extender, the more sensitive the Raman microspectrometer is to crystalline selenium.

Figure 13A:
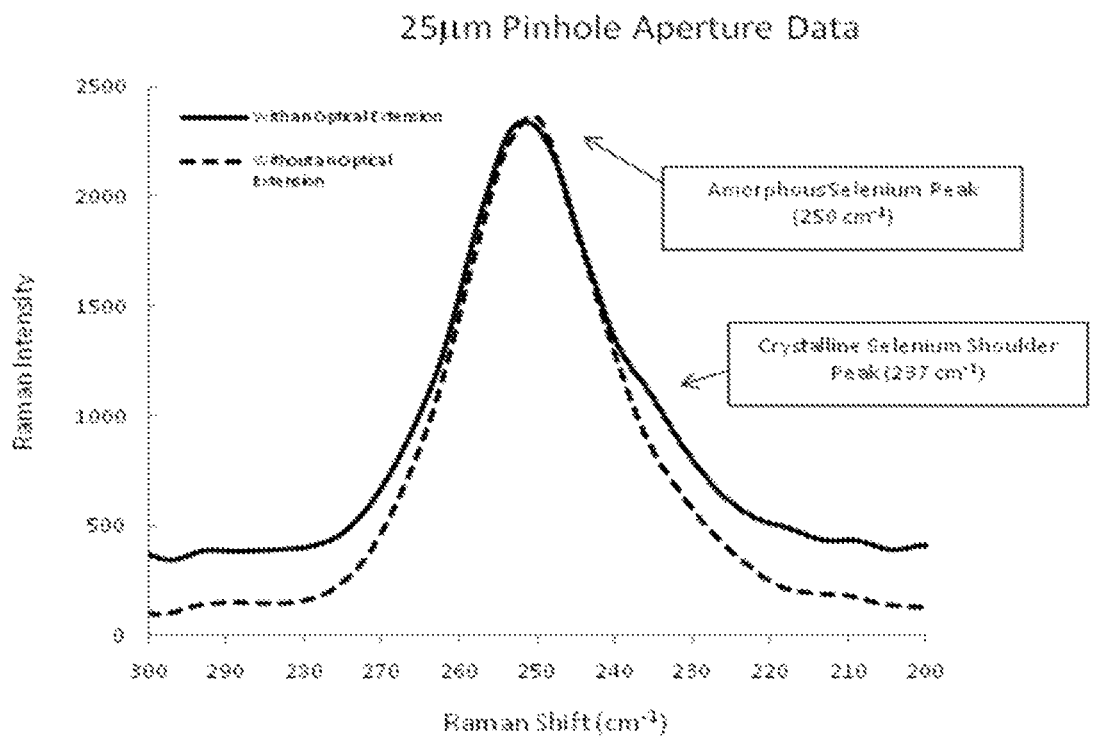
FIGS. 13A-13B show spectral analysis of a Raman microspectrometer with an optical extension and spectra of a Raman microspectrometer without an optical extension.
Figure 13B:
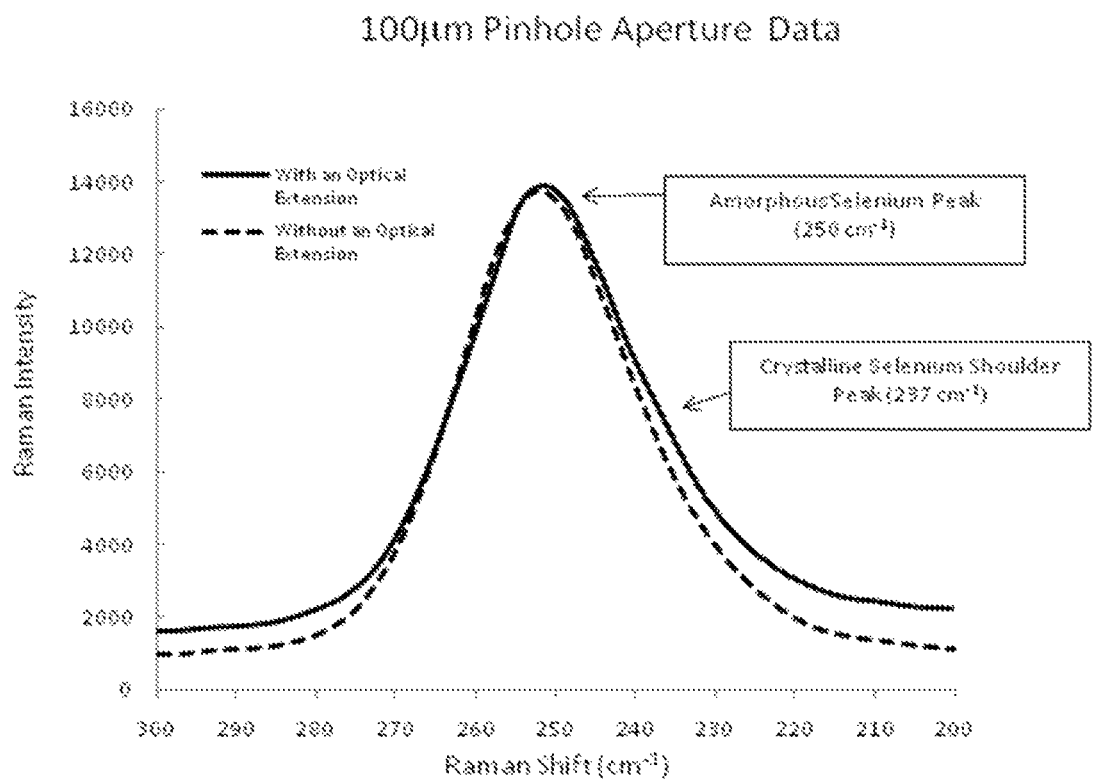

As shown in FIGS. 13A-B and described in further detail hereinbelow, As shown in FIGS. 13A-B, a Raman microspectrometer with an optical extension exhibits increased sensitivity to crystallized selenium in an otherwise amorphous selenium mammography panel compared to a Raman microspectrometer without an optical extension. It had been believed conventionally that confocal microscopy would optimize resolution and sensitivity. See Wikipedia entry for Raman spectroscopy, dated Jul. 21, 2008. An optical extension used in order to analyze an oversized sample would change the confocal aspects such that the focal length between the aperture of the Raman microspectrometer to the objective lens would be greater than the focal length between the objective lens to the oversized sample such that sensitivity would believe to be decreased. In view of what is shown herein, and at least in FIGS. 13A-B, a Raman microspectrometer with an optical extension exhibit improved sensitivity to crystalline selenium in analyzing an oversized sample with a Raman microspectrometer having an optical extension compared to a system without an optical extension. Additionally or alternatively, the Raman microspectrometer with an optical extender is configured to be less sensitive to layers above or below the focal plane.

EXAMPLE

This example describes sensitivity of a Raman microspectrometer for crystallized selenium in a mammography panel generally composed of amorphous selenium.

Sensitivity is compared between a Raman microspectrometer with an optical extension and a Raman microspectrometer without an optical extension.

TABLE 1

Conditions for Testing Sensitivity of a Raman Microspectrometer for Presence of Crystallized Selenium in an Otherwise Amorpohous Selenium Mammography Panel

| Raman Microspectrometer Parameter | With An Optical Extension (Length = 539 mm; Mirror-to-Mirror Length = 454 mm; Width = 62 mm; Height = 50 mm) | Without An Optical Extension |
| --- | --- | --- |
| Spectrometer | Almega XR | Almega XR |
| Laser | 780 nm | 780 nm |
| Laser Power Level | 3.5 mW (10% of 35 mW) | 3.5 mW (10% of 35 mW) |
| Laser Polarization | parallel | parallel |
| Cosmic Ray Threshold | low | low |
| Grating | 360 lines/mm | 360 lines/mm |
| Spectrograph Aperture for Confocality | (1) 25 µm pinhole and (2) 100 µm pinhole | (1) 25 µm pinhole and (2) 100 µm pinhole |
| Sample Position | microscope | microscope |
| CCD Camera Temperature | −49° C. | −49° C. |
| CCD Rows Binned | 1.256 | 1.256 |
| CCD Binning | on chip | on chip |
| Spectral Resolution | 1.9285 $cm^{-1}$ | 1.9285 $cm^{-2}$ |
| Total Number of Data Points | 3514 | 3514 |
| X-Axis | Raman shift ($cm^{-1}$) | Raman shift ($cm^{-1}$) |
| Y-Axis | Raman Intensity | Raman Intensity |
| First X Value | 93.4795 $cm^{-1}$ | 93.4795 $cm^{-2}$ |
| Last X Value | 3480.8311 $cm^{-1}$ | 3480.8311 $cm^{-2}$ |
| Data Spacing | 0.964233 $cm^{-1}$ | 0.964233 $cm^{-2}$ |
| Sample Format | Mammography Panel (11.288" × 9.877") with amorphous selenium | Mammography Panel (11.288" × 9.877") with amorphous selenium |
| Sample Position on Mammography Panel | gate side roll-off edge | gate side roll-off edge |
| Raman Microscope Objective | Olympus BX51TRF/UMPlanF1/ 20x/0.46 BD | Olympus BX51TRF/UMPlanF1/ 20x/0.46 BD |
| Focal Plane | lower selenium surface through support glass and TFT glass of mammography panel | lower selenium surface through support glass and TFT glass of mammography panel |

Table 1 describes the conditions for comparing a Raman microspectrometer with an optical extension and a Raman microspectrometer without an optical extension.

Use and setup of the Raman microspectometer is further described in the User's Guide for the Almega Raman spectrometer, copyright 2000, and its accompanying Almega Customer Training Manual. Under these conditions, four spectra were recorded at the same spot on the sample, i.e. (1) 25 µm pinhole aperture with an optical extension, (2) 100 µm pinhole aperture with an optical extension, (3) 25 µm pinhole aperture without an optical extension, and (4) 100 µm pinhole aperture without an optical extension. Spectra were recorded at 25 µm and 100 µm pinhole aperture selections to understand that the observed difference in crystal selenium sensitivity was not due to depth discrimination differences—as related to confocality differences—that might exist between a Raman microspectrometer with an optical extension and a Raman microspectrometer without an optical extension.

As shown in FIGS. 13A-B, spectral analysis is illustrated of an amorphous selenium mammography panel (that in this analysis includes crystallized selenium) using a Raman microspectrometer with an optical extension and without an optical extension. The solid line represents the Raman microspectrometer system with an optical extension. This system has a peak sensitivity to amorphous selenium at 250 $cm^{-1}$, and it also indicates the characteristic shoulder peak sensitivity to crystalline selenium at 237 $cm^{-1}$. In contrast, the system without an optical extension (dotted line) does not appear to have sensitivity to the crystalline selenium in at least that there is no characteristic shoulder peak. The shoulder peak illustrated for the system with an optical extension is a shoulder peak in accordance with a variety of means, e.g., peak fitting or taking the first derivative.

Accordingly a system has been shown and described which extends the functionality of existing Raman microspectrometers to enable their use with oversized samples. The system enables a process for using the supplementary stage and Raman extension for non-destructive analysis and/or repair of oversized samples such as mammography imaging panels. Such an arrangement and process greatly reduces the costs of manufacturing of mammography panels by increasing the speed and accuracy of defect characterization, and allowing such characterization to be performed without destruction of the panel. Costs are further reduced because the system can also be used to perform quick repair of the panel and return of the panel to the production line.

Having described exemplary embodiments of the invention it should be understood that such embodiments are mere representative embodiments of a system which can be used to extend an optical reach of existing molecular analysis equipment to facilitate non-destructive analysis and repair of any type of sample. It should be noted that although the specification has referred to the use of the system with an oversized sample, the present invention is not limited to use with an oversized sample, but can also accommodate samples that can also be supported by the existing stage; thus there would be no need to swap the devices of the present invention to accommodate different size samples. In addition, although several embodiments of the extension have already been shown and described, other embodiments for example where the extender is flexible, or rotatable among any axis, are also contemplated herein. In essence, any device that can be used to change the optical path of a microspectrometer to direct laser pulses on a sample that is not placed in the provided tray could be substituted herein without affecting the scope of the invention. Further, although a supplemental stage has been shown having x and y rails, other devices for supporting and moving a sample in the x, y and z axes are considered as equivalents hereto, including a circular or otherwise rotatable tray mount, etc. Further, although exemplary steps have been described for performing an analysis and or repair process using the extension, it should be appreciated that such process is not limited for use with only the components described herein.

Having described exemplary embodiments of the invention, it should be appreciated that the present invention may be achieved using other components to perform similar tasks. As described above, some aspects of the invention may be controlled by a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware.

All documents cited herein are, in the relevant part, incorporated herein by reference; the citation of any document is not to be construed as an admission that it is prior art with respect to the present invention. To the extent that any meaning or definition of a term or in this written document conflicts with any meaning or definition in a document incorporated by reference, the meaning or definition assigned to the term in this written document shall govern.

Although various exemplary embodiments of the invention have been disclosed, it should be apparent to those skilled in the art that various changes and modifications can be made that will achieve some of the advantages of the invention without departing from the true scope of the invention. These and other obvious modifications are intended to be covered by the appended claims.

What is claimed is:

1. A Raman microspectrometer system for non-destructive analysis of an oversized sample that includes amorphous selenium comprising:
   a Raman microspectrometer comprising an optical microscope coupled to a spectrometer by an optical transfer tube, the optical microscope comprising a lens and a stage; and
   an optical extender removably coupled to the optical microscope and having a proximal orifice aligned with the lens and a distal orifice, the optical extender for extending an optical reach of the microscope to the distal orifice, wherein a sensitivity of the Raman microspectrometer to some molecular vibrations corresponding to crystallized selenium is increased with the optical reach of the microscope extended and decreased with the optical reach of the microscope not extended.

2. The Raman microspectrometer of claim 1, wherein the extender comprises a plurality of mirrors including a first minor positioned adjacent to the proximal orifice and a second mirror positioned adjacent to the distal orifice, and wherein the first mirror is positioned to direct an optical signal between the proximal orifice and the second minor and the second minor is positioned to direct the optical signal between the first mirror and the distal orifice.

3. The Raman microspectrometer of claim 1 wherein a strength of the lens is adjustable.

4. The Raman microspectrometer of claim 1 further comprising a supplemental stage, coupled to a controller of the stage of the optical microscope, for moving the oversized sample along a travel distance along the at least one track in at least one of a x, y and z dimensions that exceeds a travel capability of the stage of the optical microscope in a corresponding dimension, wherein the supplemental stage comprises a motorized stage wherein travel distances of the supplemental stage correspond to a size of a mammography imaging panel.

5. The Raman microspectrometer of claim 4 wherein the supplemental stage moves along at least the z-axis and wherein the Raman microspectrometer system is configured to analyze the oversized sample at different depths.

6. The Raman microspectrometer of claim 1 wherein the extender is rotatable around the proximal orifice.

7. The Raman microspectrometer of claim 1 wherein movement of the extender is software controlled.

8. The Raman microspectrometer of claim 1 wherein the extender is a telescoping extender.

9. The Raman microspectrometer of claim 1 wherein the extender is configured to variably extend.

10. The Raman microspectrometer of claim 9 wherein movement of the extender is software controlled.

11. The Raman microspectrometer of claim 1 further comprising a lens mounting plate surrounding the distal orifice.

12. The Raman microspectrometer of claim 11 wherein the extender comprises a mounting plate positioned proximate to the proximal orifice, wherein the mounting plate conforms in shape to the lens mounting plate and wherein the mounting plate secures the extender to a lens mount of the optical microscope.

13. The Raman microspectrometer of claim 12 wherein the mounting plate is a first mounting plate, and wherein the extender further comprises a second mounting plate positioned around the distal orifice and configured to accept the lens.

14. The Raman microspectrometer of claim 1 wherein a housing of the extender comprises wave guide materials.

15. The apparatus of claim 14 wherein the waveguide materials are selected from a group including liquid optical materials and solid optical materials.

16. The Raman microspectrometer of claim 1 wherein the extender comprises a suspension arm for supporting of the extender on a body of the optical microscope.

17. The Raman microspectrometer of claim 16 wherein the suspension arm mounts to and corresponds in shape with a body of the microscope so that the suspension arm hangs from the lens.

18. The Raman microspectrometer of claim 1 wherein the system is configured to be less sensitive to layers above or below a focal plane of the system.

19. The Raman microspectrometer of claim 1 further comprising a motor disposed above the rails and operably coupled to the supplemental stage to control the movement of the supplemental stage in the x and y dimensions.

20. The Raman microspectrometer of claim 1, wherein the track is an elevated elongated structure above a base of the supplemental stage.

* * * * *